United States Patent
Ringley

(10) Patent No.: US 9,649,105 B2
(45) Date of Patent: May 16, 2017

(54) SELF SUTURING TROCAR

(71) Applicant: Chad Ringley, Saginaw, MI (US)

(72) Inventor: Chad Ringley, Saginaw, MI (US)

( * ) Notice: Subject to any disclaimer, the term of this patent is extended or adjusted under 35 U.S.C. 154(b) by 560 days.

(21) Appl. No.: 13/933,177

(22) Filed: Jul. 2, 2013

(65) Prior Publication Data

US 2015/0012017 A1    Jan. 8, 2015

Related U.S. Application Data

(62) Division of application No. 12/924,240, filed on Sep. 23, 2010, now Pat. No. 8,518,059.

(51) Int. Cl.
*A61B 17/04* (2006.01)

(52) U.S. Cl.
CPC .... *A61B 17/0469* (2013.01); *A61B 2017/047* (2013.01); *A61B 2017/0472* (2013.01)

(58) Field of Classification Search
CPC ............ A61B 17/0469; A61B 17/0482; A61B 2017/047; A61B 2017/0472
See application file for complete search history.

(56) References Cited

U.S. PATENT DOCUMENTS

| | | | | |
|---|---|---|---|---|
| 5,320,632 | A * | 6/1994 | Heidmueller | 606/144 |
| 5,374,275 | A * | 12/1994 | Bradley et al. | 606/144 |
| 6,896,685 | B1 * | 5/2005 | Davenport | 606/144 |
| 2005/0251170 | A1 * | 11/2005 | Weisenburgh et al. | 606/153 |
| 2007/0213757 | A1 * | 9/2007 | Boraiah | 606/184 |

* cited by examiner

*Primary Examiner* — Alexander Orkin

(57) ABSTRACT

A surgical incision suturing device particularly suited for minimally invasive surgical procedures comprising a suturing mechanism built into a trocar stem that enables a surgeon to stitch a patient by utilizing controls on the exposed top portion of the trocar.

4 Claims, 3 Drawing Sheets

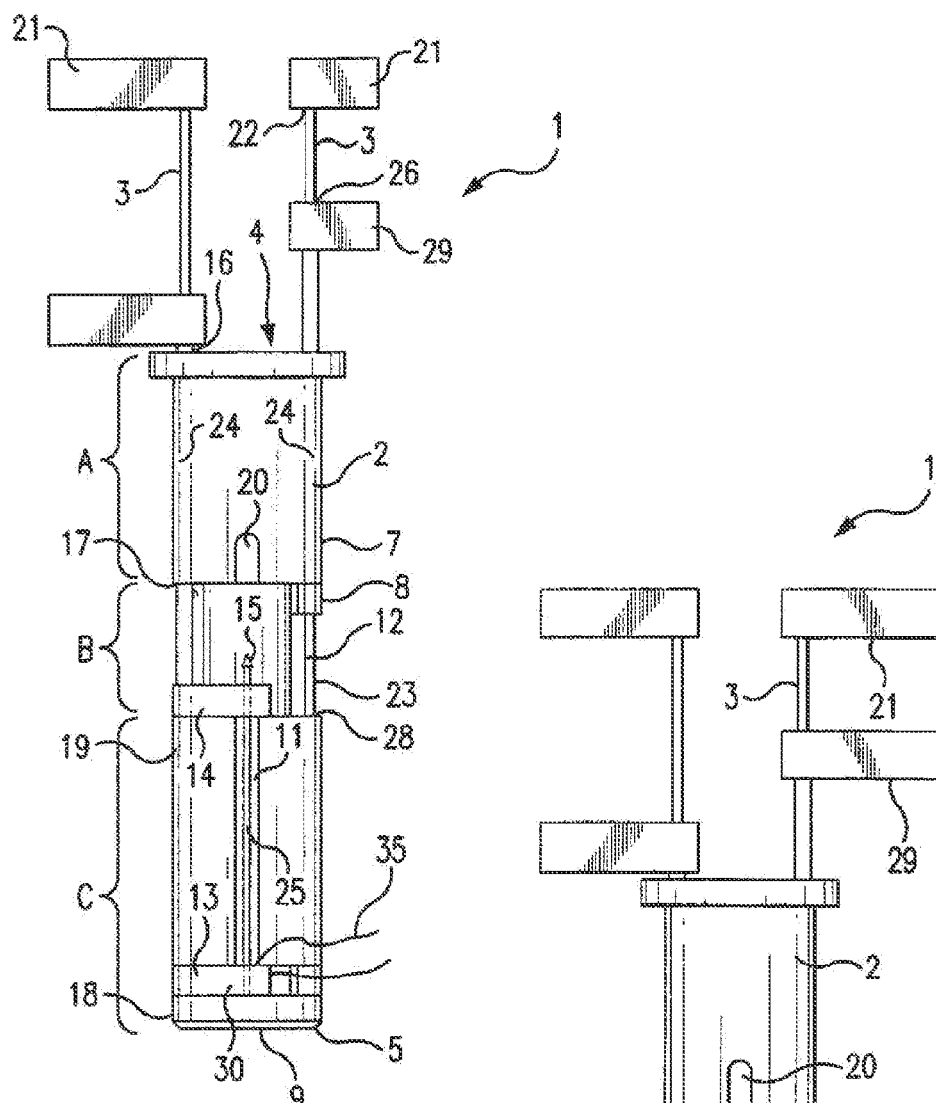
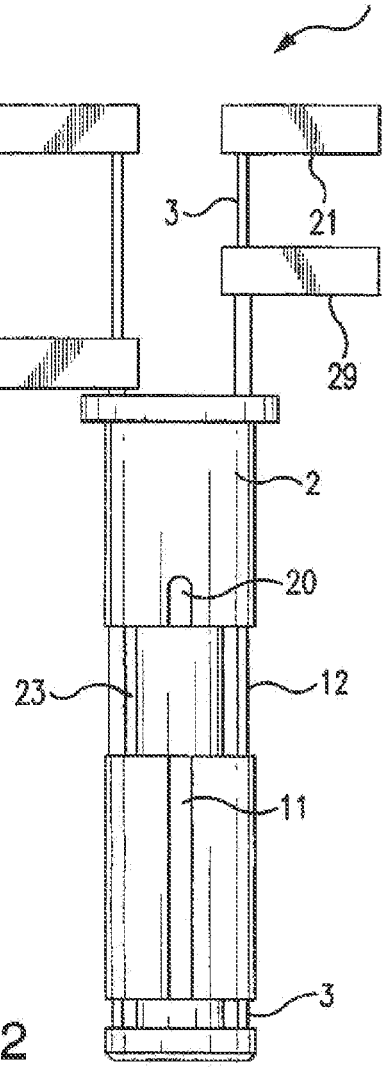
FIG. 1
FIG. 2

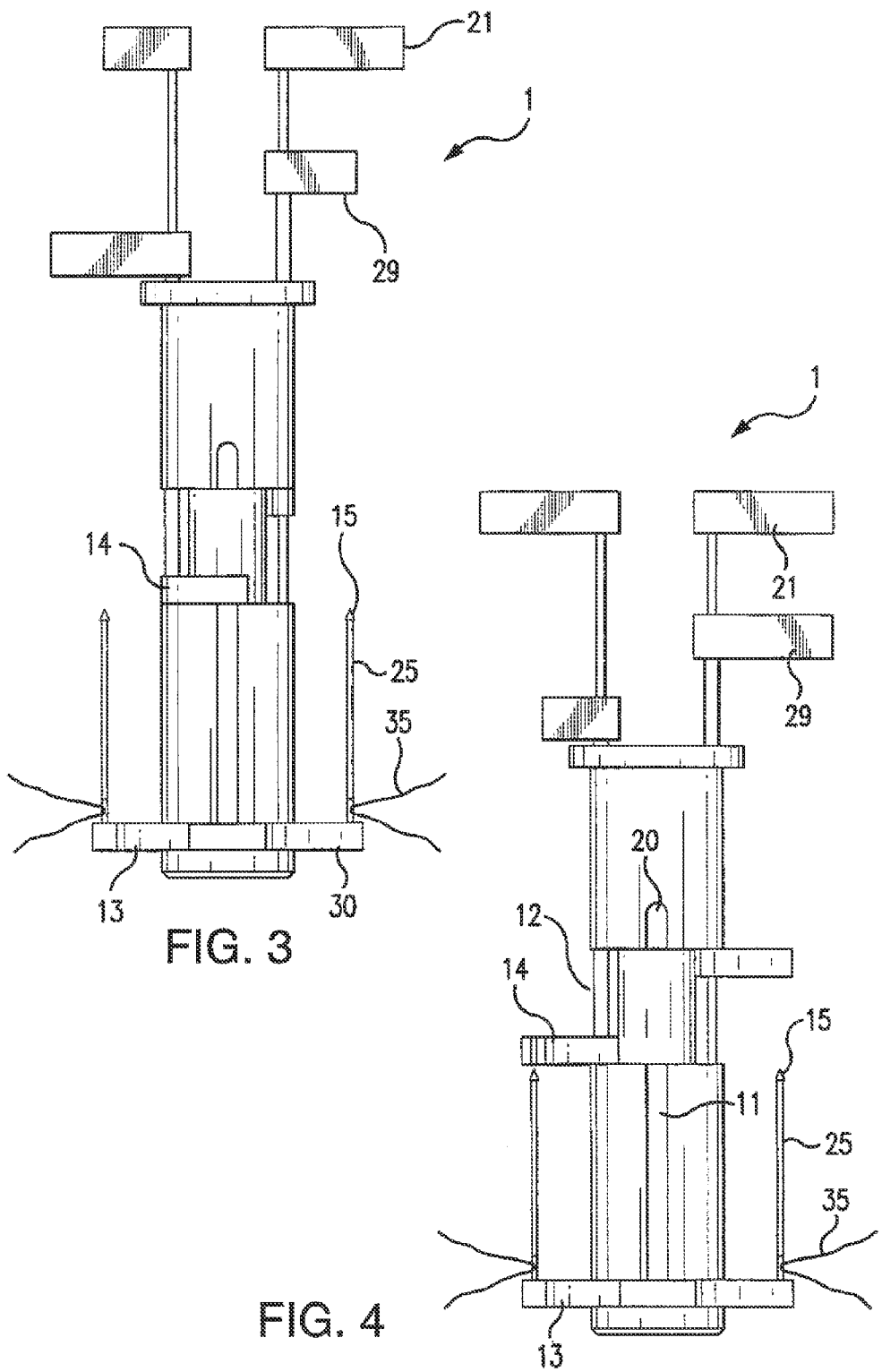

SELF SUTURING TROCAR

This application claims priority from U.S. patent application Ser. No. 12/924,240, filed Sep. 23, 2010, currently pending.

BACKGROUND OF THE INVENTION

What is disclosed and claimed herein is a surgical incision suturing device particularly suited for minimally invasive surgical procedures comprising a suturing mechanism built into a trocar stem that enables the surgeon to stitch a patient by utilizing controls on the exposed top portion of the trocar.

Currently, the most used suturing procedure requires the trocar to be removed from the body cavity. The incision is then spread apart, with an assistants help, using spreading bars and the suture is blindly hooked through the fascia tissue and tied off. The fascia, tissue is located directly beneath the body fat and surrounds the muscle. The fascia is what holds the suture in place and provides the needed strength. The blind suturing procedure takes up to 30 minutes or more to complete in a two hour surgical procedure. The means that roughly 25% of the entire procedure is consumed by the suturing process, and it is vital for the patient be under anesthetic for a minimal amount of time.

The trocar of the instant invention makes a single suture through the fascia tissue by simply pulling the trocar up and out. The two ends of the surgical suturing thread will then be tied off by the surgeon in order to complete the stitch. This new invention will decrease the time it takes to complete each surgery, thus reducing the time the patient is under anesthetic as well as minimizing the chance of trocar herniation. Because of safety concerns, space constraints, ease of use, and small scale, the device of the instant invention is simple to use.

The device permits the suturing of the patients' fascia as a result of pulling up the trocar, reducing the overall surgery time, and simplifying the general surgery procedure.

THE INVENTION

Thus, in one embodiment, this invention deals with a self suturing trocar that comprises a suturing mechanism built into a trocar stem that enables the surgeon to stitch a patient.

Therefore, there is provided in one embodiment a self suturing trocar, wherein Trocar comprises a thick-walled, round, unitary housing having a centered opening through it and an outside surface on the housing.

The housing has three sections, a top section, a middle section and a bottom section, wherein the bottom section comprises a near end and a distal end. There is a circumferential narrow groove in the surface of the bottom section of the housing and near the distal end, and a set of two oppositely opposed vertical grooves extending from the circumferential groove, through the near end.

The middle segment comprises a broad circumferential groove in the housing.

The top segment comprises a top edge and a bottom edge, a near end and a distal end and there are two oppositely opposed vertical notches at the near end beginning at the broad circumferential groove in the housing.

There are two oppositely opposed solid shafts rotatably held in the bottom segment of the housing and extending from the distal end to a terminus, a predetermined distance beyond the top edge of the top section, wherein each top terminus has a first turn lever fixedly mounted thereon and each hollow shaft has a second turn lever fixedly mounted at the top.

Each hollow shaft has a needle holder fixedly mounted at the bottom end and each solid shaft has a needle support mounted near the distal end of the bottom section and in the circumferential narrow groove.

Each hollow shaft is capable of moving up and down within the housing a distance determined by the width of the broad circumferential groove, thereby providing a capability of moving the needle holder a distance determined by the width ox the broad circumferential broad groove.

There is the top turning lever that is capable of moving the needle support in a horizontal movement and a bottom turning lever that is capable of moving the needle holder in a horizontal movement.

In another embodiment, there is provided a method of suturing tissue, the method comprising inserting a pre-prepared trocar of as described just Supra, into an opening in the tissue, wherein suture needles have been inserted into the opening in the needle support and wherein the needles have been equipped with suture material, and wherein the needle supports, needle holders and needles have been inserted into the circumferential grooves and vertical grooves.

Thereafter, each trocar is provided with at least one suture for the tissue, and thereafter, the prepared sutures are tied off.

There is yet another embodiment, that comprises a method of suturing tissue. The method comprises providing an opening in the tissue to accommodate a trocar, providing a trocar as described Supra that has been pre-prepared by threading suture thread into eyes of each needle. Each needle has an enlarged forward piercing tip. The base of each needle is inserted into a needle support arm, and the needle support containing said needle is closed into the narrow circumferential groove in the bottom segment.

The trocar is inserted into the opening in the tissue and below the bottom of the tissue and each top turn lever is twisted horizontally to move the needle support arms and to remove the suturing needle that is contained therein from each vertical groove which exposes the suture needles.

The trocar is pulled upwards toward the bottom of the tissue to be sutured, piercing through the tissue and then the bottom turn lever is twisted horizontally to move each needle holder arm in alignment with the tip of a suturing needle.

Each bottom turn lever is then pushed downwardly to allow each needle holder arm to contact and enclose a needle tip and then the bottom, turn lever is pushed towards the centered opening which rotates the hollow shaft, which in turn moves the needle holder horizontally into the broad circumferential groove.

Then the trocar is withdrawn from the incision and, the exposed ends of the suture thread are grasped and tied off to complete the suture.

BRIEF DESCRIPTION OF THE DRAWINGS

FIG. 1 is a full side view of a device of this invention as it is ready for insertion into an incision.

FIG. 2 is a full side view of a device of this invention without the needles, needle holders, and needle supports to show the construction of the housing and shafts.

FIG. 3 is a full side view of a device of this invention in which the needles are in the needle supports and are disposed for use within the tissue.

FIG. 4 is a full side view of a device of this invention wherein, the piercing of the tissue has taken place, and the needle holders have been positioned to receive the needles.

DETAILED DESCRIPTION OF THE DRAWINGS

Figure 5:
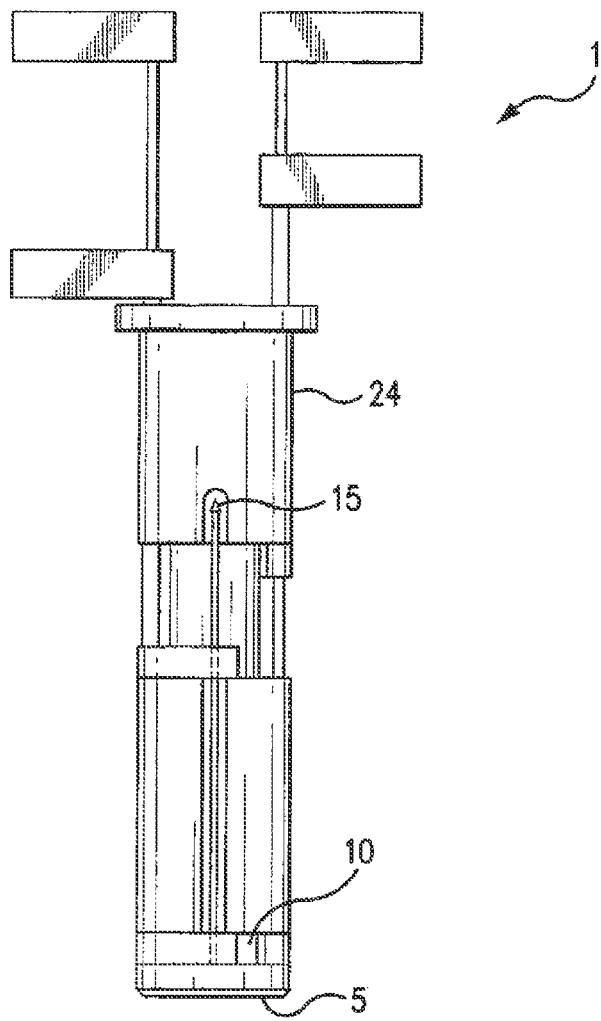
FIG. 5 is a full side view of a device of this invention in which the needles have been inserted into the needle holders and the turn levers raised to place the tips of the needles in the notch.

Turning now to FIG. 1 which is a full side view of a device 1 of this invention as it is ready for insertion into an incision (a pre-prepared trocar).

There is shown the thick-walled housing 2. It is unitary in construction, meaning that it is a single piece. By "thick-walled", it is meant herein that the walls cannot be flimsy as they support the solid shafts 3 and the thick-walled housing 2 must be able to allow for the movement of the solid shafts 3 and 3' to be moved up and down through the wall. Thus, the wall must be thick enough to provide room for an opening from the top 4 to the bottom 5 of the housing 2 and further, the wall must have enough strength to allow for the insertion and removal of the trocar 1. For purposes of this invention, thick means on average, a wall thickness of from about ⅛ inch to about ½ inch keeping in mind that the trocar 1 has to fit into a minimal opening during surgery. Likewise, the trocar 1 has an overall average length of from about 2½ inches to about 6 inches, but can be made longer or shorter depending on the type of surgery to be performed and the wall thickness can be determined by the type of surgery to be performed.

There is a centered opening 6 through the long axis of the trocar 1 such that other surgical instruments, lights, cameras, and other suitable equipment can be inserted therein to accommodate the particular surgery being performed using said trocar.

The housing 2 has an outside surface 7, for which use will be set forth infra. The housing 2, for purposes of simple-explanation, has, generally three sections, the top section generally denoted as "A" in FIG. 1, the middle section generally denoted as "B" in FIG. 1, and the bottom section generally denoted as "C" in FIG. 1.

The bottom section C comprises a near end 8 and a distal end 9, wherein there, is a circumferential narrow groove 10 (FIG. 5) in the surface of the housing 2, and near the distal end 9. There is a set of two, oppositely opposed vertical grooves 11 extending from the circumferential groove 10 through 15 the near end 8 (opposite groove 11 not shown).

The middle segment B comprises a broad circumferential groove 12 in the housing. For purposes of this invention, "narrow" means that the circumferential groove 10 is narrower in width that the broad circumferential groove 12. Further, "broad" means a width of the groove on the order of from ¼ inch to 1 inch and "narrow" means a width of the groove on the order of from ⅛ inch to about 3/16 inches.

The depth of such circumferential grooves 11 and 12 must be such that they will accommodate the components that are insertable in them, such as the support arms 13 in the narrow groove 10 and the guide arms 14 and a portion of the needle tips 15 that are insertable in the broad groove 12, and the short vertical notches 20.

The top section A comprises a top edge 16 and a bottom edge 17, a near end 18 and a distal end 19. There are two oppositely opposed vertical notches 20 at the near end 18 beginning at the broad circumferential groove 12 in the housing 2.

There are two oppositely opposed solid shafts 3 rotatably held in the outside wall 24 of the housing 2 and they rotate in openings 27 at their bottom ends 31, in the distal end 9 of bottom segment C of the housing 2 and they extend from the distal end 9 to a terminus 22, which is a predetermined distance beyond the top edge 16 of the top section A. Each top terminus 22 has a first turn lever 21 fixedly mounted thereon.

There is a hollow shaft 23 mounted over each of the solid shafts 3, each said hollow shaft having a bottom end 28 and a length essentially equivalent to the length of section A plus the width of the broad circumferential groove 12. There is fixedly attached to the top 26 of each hollow shaft 23, a second turn lever 29 that swivels the hollow shaft 23. Each solid shaft 3 has a needle holder 30 fixedly mounted thereon at the bottom end 31 such that when the second turn lever 29 is swiveled, the needle holder 30 rotates.

Each hollow shaft 23 is movable up and down in a vertical fashion within the outside wall 24 of the housing 2. As indicated Supra, this movement is restricted to a distance equivalent to the width of the broad circumferential groove 12, as the there is a necessity of moving any needle held therein to move up and down vertically.

Each solid shaft 3 has a needle support 13 mounted near the distal end 9 of the bottom section C, said needle support 13 insertable into the narrow circumferential groove 10 and removable therefrom by turning the respective solid shaft 3 which is rotated using the first (top) turn lever 21. The top turn lever 21 is capable of moving the needle support 13 in a rotational horizontal movement while the bottom turning lever 29 is capable of moving the needle guide arms 14 in a rotational horizontal movement.

As set forth Supra, FIG. 1 is a full side view of a device of this invention as it is ready for insertion into an incision showing the location of the needles 25 (only one shown) as being supported by the needle support 13, and held in needle guide arms 14. The needles 25, needle support 13 and the needle guide arms 14 are all fitted into the broad circumferential groove 12 and the narrow circumferential groove 10 in preparation for insertion of the device into an incision.

It should be noted that the first turning lever 21 is distal from the second turning lever 29, which rests on the top edge 16 of section A. There is also shown suture threads 35 in this Figure. The needle is fitted in the vertical groove 11 in the bottom section C.

FIG. 2 is a full side view of a device of this invention without the needles, needle holders, and needle supports to show the construction of the housing and shafts, wherein there is shown the housing 2, the broad circumferential groove 12 in which there is shown the hollow shafts 23, the vertical groove 20 in section A, the vertical grooves 11 in section C, and the solid shafts 3 at both the top and the bottom of the device. It should be noted that this FIG. 2 is representative of FIG. 1 in a "ready to use" configuration, minus the aforementioned components for clarity.

FIG. 3 is a full side view of a device of this invention in which the needles are in the needle supports and are disposed for use within the tissue after the insertion in the incision and are deployed.

FIG. 4 is a full side view of a device of this invention wherein, the piercing of the tissue has taken place, and the needle holders and guide arms 14 have been positioned to receive the needles. In order to ready the device for removal from the incision, the turning levers 21 and 29 are pulled upwards which allows the needles 25 to insert into the guide and holder arms 14 and then, the guide arms 14 and the needles are turned into the broad circumferential groove 12, the vertical grooves 11 and the support arms 13 turn into the narrow circumferential groove 10 to close the device.

FIG. 5 is a full side view of a device 1 of this invention in which the needles 25 have been inserted into the needle supports 13 and the needle guides 14 and turned into the grooves to place the tips of the needles in the notch 20 wherein the device can now be removed from the incision.

Figure 6:
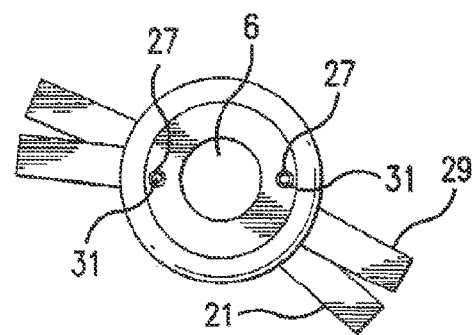
FIG. 6 is a full bottom view of a device of this invention.

FIG. 6 is a full bottom view of a device of this invention showing the centered openings 6, the first turn lever 29 and the second turn lever 21 along with the openings 27 and the bottom ends 31 of the solid shafts 3.

In another embodiment of this invention, there is a method of suturing tissue, said method comprising providing an opening in the tissue to accommodate a trocar. Thereafter, providing a trocar as described in detail Supra that has been pre-prepared by threading suture thread into eyes of each needle wherein each needle has an enlarged forward piercing tip.

Thereafter, inserting the base of each needle into a needle support arm, and closing the needle support containing said needle into the narrow circumferential groove in the bottom section. Thereafter, inserting the trocar into the opening in the tissue and below the bottom of the tissue and twisting each top turn lever to move the needle support arms to remove the suturing needle that is contained therein from each vertical groove and thereby exposing the suture needles.

Thereafter, pulling the trocar upwards toward the bottom of the tissue to be sutured, piercing through the tissue and twisting the bottom turn lever to move each needle holder arm in alignment with the tip of a suturing needle.

Thereafter, pushing each bottom turn lever downwardly to allow each needle holder arm to contact and enclose a needle tip and thereafter plashing the bottom turn lever towards the centered opening which rotates the hollow shaft, which in turn moves the needle holder horizontally into the broad circumferential groove.

Finally, withdrawing the trocar and, grasping any exposed ends of the suture thread and tying off.

What is claimed:

1. A method of suturing tissue, said method comprising:
   A. providing an opening in said tissue to accommodate a trocar;
   B. providing a trocar, said trocar comprising a trocar that has been pre-prepared by threading suture thread into eyes of each needle, each said needle having an enlarged forward piercing tip;
   C. inserting a base of each said needle into a needle support arm, and closing said needle support arm containing said needle in a narrow circumferential groove in a bottom segment;
   D. inserting said trocar into an opening in said tissue and below a bottom of the tissue;
   E. twisting a top turn lever to move said needle support arm and to remove a suturing needle that is contained therein from each vertical groove and thereby exposing each suturing needle;
   F. pulling said trocar upwards toward said bottom of said tissue to be sutured, piercing through said tissue;
   G. twisting a bottom turn lever to move each said needle holder arm in alignment with a tip of a suturing needle;
   H. pushing each said bottom turn lever downwardly to allow each said needle holder arm to contact and enclose a needle tip;
   I. pushing said bottom turn lever towards a centered opening of the trocar which rotates a hollow shaft, which in turn moves said need holders horizontally into a broad circumferential groove;
   J. withdrawing said trocar and, grasping any exposed ends of said suture thread and tying off.

2. The method of suturing tissue as claimed in claim 1 where a suture supply is held with the trocar.

3. The method of suturing tissue as claimed in claim 1 wherein a suture supply is contained with the trocar.

4. A method of suturing tissue, said method comprising:
   (A.) utilizing a trocar, said trocar comprising: a thick-walled round, unitary housing having a centered opening therethrough and an outside surface; said housing having three sections, a top section, a middle section and a bottom section;
   said bottom section comprising a near end and a distal end, wherein there is a circumferential narrow groove in the surface of said housing and near said distal end, and a set of two oppositely opposed vertical grooves extending from said circumferential groove through said near end;
   said middle segment comprising a broad circumferential groove in said housing;
   said top segment comprising a top edge and a bottom edge, a near end and distal end wherein there are two oppositely opposed vertical notches at said near end beginning at said broad circumferential groove in said housing;
   two oppositely opposed solid shafts rotatably held in a bottom segment of said housing and extending from said distal end to a terminus, a predetermined distance beyond a top edge of a top section each said solid shaft being mounted in a hollow shaft;
   each top terminus having a first turn lever fixedly mounted thereon;
   each said hollow shaft having a second turn lever fixedly mounted at a top thereon;
   each said hollow shaft having a needle holder fixedly mounted thereto at said bottom end;
   each said solid shaft having a needle support mounted near said distal end of said bottom section and in said circumferential narrow groove;
   each hollow shaft being capable of moving up and down within said housing, a distance determined by the width of said broad circumferential groove, thereby providing a capability of moving said needle holder a distance determined by the width of said circumferential broad groove;
   said first turning lever being capable of moving said needle support in a horizontal movement;
   said second turning lever being capable of moving said needle holder in a horizontal movement;
   (B.) proving an opening in said tissue to accommodate the trocar;
   (C.) providing said trocar, wherein said trocar has been pre-prepared by threading suture thread into eyes of each needle, each said needle having an enlarged forward piercing tip;
   (D.) inserting a base of each said needle into a needle support arm, and closing said needle support containing said needle into the said narrow circumferential groove in said bottom segment;
   (E.) inserting, said trocar into said opening in said tissue and below said bottom of said tissue;
   (F.) twisting each top lever to move said needle support arms and to remove said needle that is contained therein from each vertical groove and thereby exposing said needle;

(G.) pulling said trocar upwards toward said bottom of said tissue to be sutured, piercing through said tissue;

(H.) twisting said bottom turn lever to move each said needle holder arm in alignment with a tip of each said needle;

(I.) pushing each said bottom turn lever downwardly a to allow each said needle holder arm to contact and enclose a needle tip;

(J.) pushing said bottom turn lever towards said centered opening which rotates said hollow shaft, which in turn moves said need holders horizontally into said broad circumferential groove;

(K.) withdrawing said trocar and, grasping an exposed ends of said suture thread and tying off.

* * * * *